US011382862B2

(12) United States Patent
Fedorchak et al.

(10) Patent No.: US 11,382,862 B2
(45) Date of Patent: Jul. 12, 2022

(54) GEL FOR TREATING PERIOCULAR AND/OR ORBITAL PATHOLOGIES AND CONDITIONS

(71) Applicant: University of Pittsburgh—Of the Commonwealth System of Higher Education, Pittsburgh, PA (US)

(72) Inventors: Morgan V. Fedorchak, Mars, PA (US); Jenny Yu, Pittsburgh, PA (US); Michael A. Washington, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 100 days.

(21) Appl. No.: 16/764,285

(22) PCT Filed: Nov. 15, 2018

(86) PCT No.: PCT/US2018/061227
§ 371 (c)(1),
(2) Date: May 14, 2020

(87) PCT Pub. No.: WO2019/099630
PCT Pub. Date: May 23, 2019

(65) Prior Publication Data
US 2020/0360282 A1 Nov. 19, 2020

Related U.S. Application Data

(60) Provisional application No. 62/587,270, filed on Nov. 16, 2017.

(51) Int. Cl.
*A61K 9/06* (2006.01)
*A61K 9/00* (2006.01)
(Continued)

(52) U.S. Cl.
CPC .............. *A61K 9/06* (2013.01); *A61K 9/0048* (2013.01); *A61K 31/573* (2013.01); *A61K 47/32* (2013.01);
(Continued)

(58) Field of Classification Search
CPC ...... A61K 9/06; A61K 9/0048; A61K 31/573; A61K 47/32; A61K 47/36; A61K 27/16;
(Continued)

(56) References Cited

U.S. PATENT DOCUMENTS 6,486,213 B1 11/2002 Chen et al.
6,737,448 B2 5/2004 Liao
(Continued)

FOREIGN PATENT DOCUMENTS

WO       201715449    * 9/2017
WO     2017165449 A1 * 9/2017
WO    WO 2017/165449    9/2017

OTHER PUBLICATIONS

Schittkowski et al., "Injectable self inflating hydrogel pellet expanders for the treatment of orbital volume deficiency in congenital microphthalmos: preliminary results with a new therapeutic approach," *British Journal of Ophthamology*, vol. 90, pp. 1173-1177, Aug. 23, 2006.

(Continued)

*Primary Examiner* — Carlos A Azpuru
(74) *Attorney, Agent, or Firm* — Klarquist Sparkman, LLP

(57) ABSTRACT

A method comprising treating a periocular wound in a subject, comprising topically administering to the periocular wound a composition comprising at least one thermoresponsive gel.

17 Claims, 2 Drawing Sheets

(51) Int. Cl.
  *A61K 31/573* (2006.01)
  *A61K 47/32* (2006.01)
  *A61K 47/36* (2006.01)
  *A61L 27/16* (2006.01)
  *A61L 27/26* (2006.01)
  *A61L 27/52* (2006.01)
  *A61L 27/54* (2006.01)

(52) U.S. Cl.
  CPC ............... *A61K 47/36* (2013.01); *A61L 27/16* (2013.01); *A61L 27/26* (2013.01); *A61L 27/52* (2013.01); *A61L 27/54* (2013.01); *A61L 2300/222* (2013.01); *A61L 2430/16* (2013.01)

(58) Field of Classification Search
  CPC .......... A61L 27/26; A61L 27/52; A61L 27/54; A61L 2300/222; A61L 2430/16; A61L 2300/25; A61L 2300/252; A61L 2300/256; A61L 2300/404; A61L 2300/41; A61L 2300/622; A61L 2400/06; A61L 27/18; A61P 27/00; C08F 220/54
  See application file for complete search history.

(56) References Cited

U.S. PATENT DOCUMENTS

| | | | |
|---|---|---|---|
| 2006/0134050 A1* | 6/2006 | Griffith | A61K 35/12 424/70.16 |
| 2014/0018323 A1 | 1/2014 | Friedman et al. | |
| 2015/0374633 A1 | 12/2015 | Fedorchak et al. | |
| 2016/0220725 A1* | 8/2016 | Whalen, III | A61L 24/0015 |
| 2019/0099365 A1 | 4/2019 | Fedorchak et al. | |

OTHER PUBLICATIONS

Da Silva et al., "Intraorbital polyacrylamide gel injection for the treatment of enophthalmos," *Ophthalmic Plastic Reconstructive Surgery*, 24(5): 367-371, Oct. 31, 2008. (abstract only).

International Search Report and Written Opinion issued for International Application No. PCT/US2018/061227 dated Feb. 26, 2019.

\* cited by examiner

GEL FOR TREATING PERIOCULAR AND/OR ORBITAL PATHOLOGIES AND CONDITIONS

CROSS REFERENCE TO RELATED APPLICATIONS

This is the U.S. National Stage of International Application No. PCT/US2018/061227, filed on Nov. 15, 2018, which was published in English under PCT Article 21(2), which application in turn claims the benefit of U.S. Provisional Appl. No. 62/587,270, filed Nov. 16, 2017, which is incorporated herein by reference in its entirety.

BACKGROUND

Proper preservation and protection of a traumatic periocular wound are critical to preventing or mitigating further damage of the affected ocular tissue(s). The current methodologies for treating such wounds are limited to applying wet or dry gauze which have been shown to transmit pressure to the eye.

Enophthalmia describes a posterior displacement of the eye within the orbit, which can be congenital or acquired as a result of trauma or disease. For example, enophthalmia may be caused by a degeneration and shrinking of the orbital fat, a tumor, an injury to the orbit or to shortening of the extraocular muscles following excessive resections. While biodegradable gel fillers can be used as a temporary means of raising the eye in the orbit, these materials will typically be resorbed within 12 months and require repeat injections. In the case of enophthalmia secondary to ocular trauma, one of the causes of lingering enophthalmia is thought to be late surgical intervention, often delayed due to excessive swelling.

SUMMARY

Disclosed herein is a method comprising treating a periocular wound in a subject, comprising topically administering to the periocular wound a composition comprising at least one thermoresponsive gel.

Further disclosed herein is a method for treating an ocular condition associated with an orbit in a subject, comprising intraorbitally administering to the subject in need thereof a composition comprising at least one non-degradable stimuli-responsive gel.

Also disclosed herein is a method comprising providing orbital volume filling or mechanical support for an eye or a combination of both wherein the method comprises intraorbitally administering to a subject in need thereof a composition comprising at least one thermoresponsive gel.

Additionally disclosed herein is a method comprising treating an ocular condition or periocular condition in a subject, comprising administering to the subject in need thereof a composition comprising a thermoresponsive gel, wherein the thermoresponsive gel comprises a copolymer of (a) N-isopropylacrylamide, (b) at least one comonomer selected from ethyl acrylate, acryloxysuccinimide, or (R)-α-acryloyloxy-β,β-dimethyl-γ-butyrolactone, and optionally (c) at least one additional monomer or crosslinker.

Further disclosed herein is a method comprising treating an ocular condition or periocular condition in a subject, comprising administering to the subject in need thereof a composition comprising a thermoresponsive gel, wherein the thermoresponsive gel comprises:

a copolymer of (a) N-isopropylacrylamide and (b) at least one acrylic monomer or at least one methacrylic monomer; and at least one additional additive selected from a poly (siloxane), a bisacrylamide, a dimethacrylate, a polysaccharide, or a combination thereof.

The foregoing will become more apparent from the following detailed description, which proceeds with reference to the accompanying figures.

DETAILED DESCRIPTION

Terminology

Figure 1:
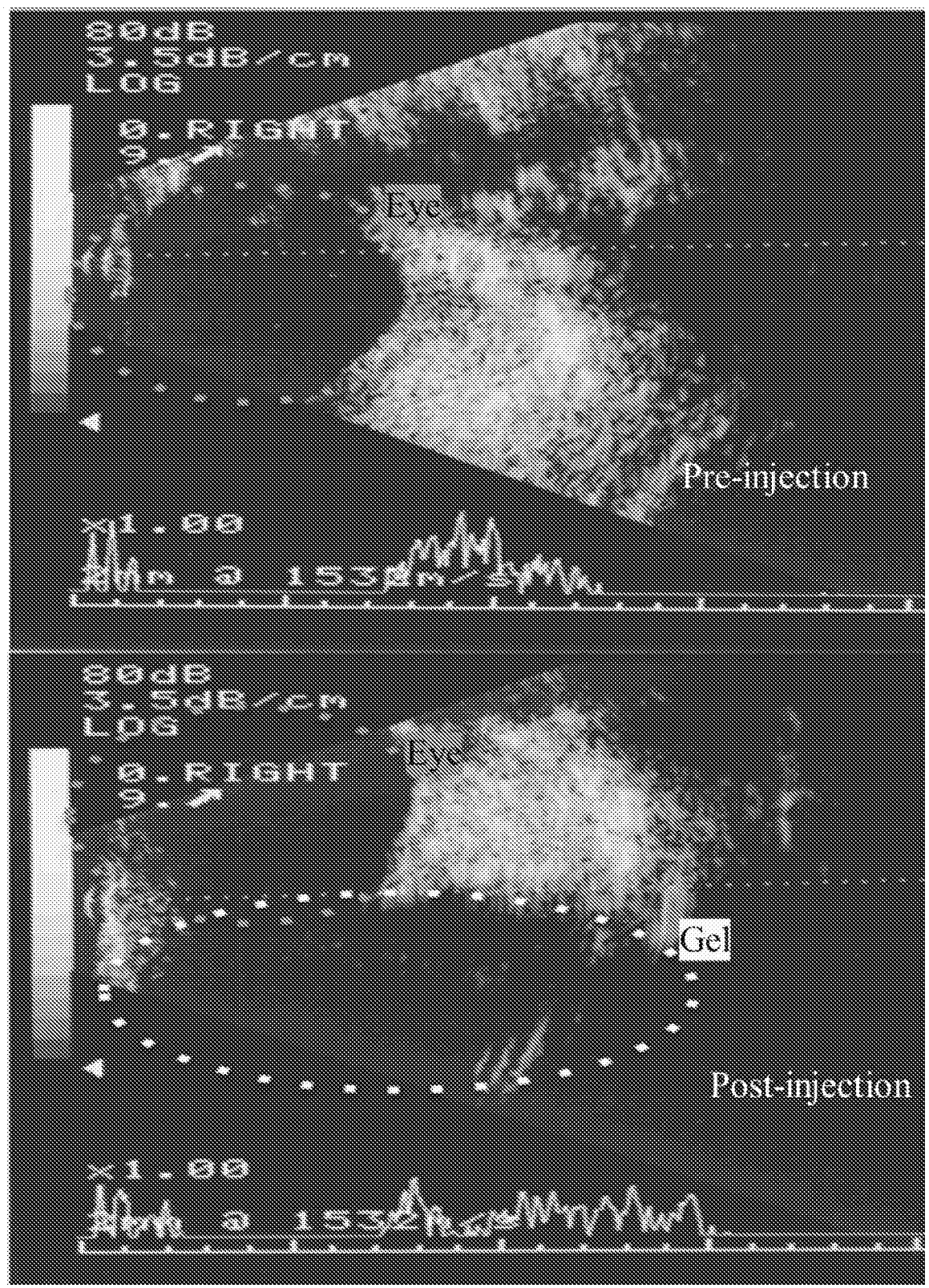
FIG. 1 shows the repositioning of rabbit globe using intraorbital pNIPAAM-co-EA gel as disclosed herein.
Figure 2:
FIG. 2 shows a rabbit debridement model (top) and space-filling placement of a gel composition as disclosed herein.

The following explanations of terms and methods are provided to better describe the present compounds, compositions and methods, and to guide those of ordinary skill in the art in the practice of the present disclosure. It is also to be understood that the terminology used in the disclosure is for the purpose of describing particular embodiments and examples only and is not intended to be limiting.

An "animal" refers to living multi-cellular vertebrate organisms, a category that includes, for example, mammals and birds. The term mammal includes both human and non-human mammals. Similarly, the term "subject" includes both human and non-human subjects, including birds and non-human mammals, such as non-human primates, companion animals (such as dogs and cats), livestock (such as pigs, sheep, cows), as well as non-domesticated animals, such as the big cats.

The term "co-administration" or "co-administering" refers to administration of an agent disclosed herein with at least one other therapeutic or diagnostic agent within the same general time period, and does not require administration at the same exact moment in time (although co-administration is inclusive of administering at the same exact moment in time). Thus, co-administration may be on the same day or on different days, or in the same week or in different weeks. In certain embodiments, a plurality of therapeutic and/or diagnostic agents may be co-administered by encapsulating the agents within the microparticles disclosed herein.

"Inhibiting" refers to inhibiting the full development of a disease or condition. "Inhibiting" also refers to any quantitative or qualitative reduction in biological activity or binding, relative to a control.

"Microparticle", as used herein, unless otherwise specified, generally refers to a particle of a relatively small size, but not necessarily in the micron size range. In certain embodiments, microparticles specifically refers to particles having a diameter from about 1 to about 25 microns, preferably from about 10 to about 25 microns, more preferably from about 10 to about 20 microns. In one embodiment, the particles have a diameter from about 1 to about 10 microns, preferably from about 1 to about 5 microns, more preferably from about 2 to about 5 microns. As used herein, the microparticle encompasses microspheres, microcapsules, or microparticles, unless specified otherwise. A microparticle may be of composite construction and is not necessarily a pure substance; it may be spherical or any other shape.

A "therapeutically effective amount" refers to a quantity of a specified agent sufficient to achieve a desired effect in a subject being treated with that agent. Ideally, a therapeutically effective amount of an agent is an amount sufficient to inhibit or treat the disease or condition without causing a substantial cytotoxic effect in the subject. The therapeutically effective amount of an agent will be dependent on the subject being treated, the severity of the affliction, and the manner of administration of the therapeutic composition. For example, a "therapeutically effective amount" may be a level or amount of agent needed to treat enophthalmia without causing significant negative or adverse side effects to the eye or a region of the eye.

"Treatment" refers to a therapeutic intervention that ameliorates a sign or symptom of an abnormal physical condition caused by trauma, a disease, or a pathological condition, after it has begun to develop, or administering a compound or composition to a subject who does not exhibit signs of a disease or exhibits only early signs for the purpose of decreasing the risk of developing a pathology or condition, or diminishing the severity of a pathology or condition. As used herein, the term "ameliorating," with reference to an abnormal physical condition caused by trauma, a disease or a pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, an improvement in the overall health or well-being of the subject, improved physical condition, or by other parameters well known in the art that are specific to the particular disease. The phrase "treating a disease" refers to inhibiting the full development of a disease. "Preventing" a disease or condition refers to prophylactic administering a composition to a subject who does not exhibit signs of a disease or exhibits only early signs for the purpose of decreasing the risk of developing a pathology or condition, or diminishing the severity of a pathology or condition. In certain embodiments, "treating" means reduction or resolution or prevention of vision loss or poor aesthetic outcomes.

Disclosed herein are stimuli-responsive materials for orbital and/or ocular treatment. In certain embodiments, the material is in the form of a gel, particularly a hydrogel. In certain embodiments, the hydrogel may have a water content of greater than 80%, or greater than 85%, or greater than 90%, or more particularly greater than 95%.

In certain embodiments, the gel disclosed herein may be topically administered for treating periocular wounds. The periocular region is the space near the globe itself. It is defined as the soft tissue within the bony walls of the orbit. The periocular region includes eyelids, lacrimal system, mid-face, brow, and the canthal region. In certain embodiments, the gel is topically administered for treating only a periocular wound. In other embodiments, the gel is topically administered to simultaneously treat both a periocular wound and an ocular wound. For example, the gel may be topically administered to treat an acute periocular wound and an ocular wound. The gel may be utilized by a first responder to treat a victim to stabilize the wound while the patient waits for further treatment (e.g., surgery). For instance, the hydrogel may be in place over the wound for a time period of not more than 168 hours, particularly not more than 72 hours.

The gel has certain advantageous properties that enable application by a first responder. The advantageous properties include a potential liquid to gel transition (caused by incorporation of thermoresponsive agents in the polymer network), defect-free space filling of lacerations and other injuries due to the rheological properties such as viscosity and phase transition temperature and time, in certain embodiments adhesion to the eye or periocular area caused by incorporation of polysaccharides into the gel and/or in situ crosslinking capabilities to improve stability, adhesion, and mechanical properties.

For example, the topically administered gel material transitions from a clear liquid to an opaque solid upon dermal application. The transparency of the liquid precursor can still allow for visualization of the wound during application. The transition to an opaque gel allows for clear visualization of all applied material, making it obvious that treatment has been administered. Upon removal visual inspection for opaque gel material may help prevent incomplete removal or residual material. This material can be fully degradable, resistant to degradation, or fully non-degradable, conforms to the volume of the tissue defect without introducing occlusions, and may be removed via irrigation with a saline solution or temperature decrease to force phase transition back to liquid, or it may be removed with temperature increase and manual removal by hand or with a handheld tool such as forceps A further benefit of the compositions disclosed herein include drug release capabilities in which therapeutic drugs (e.g. antiinflammatory, antibiotic, analgesic, etc. . . . ) can be released into the damaged tissue(s) via absorbed drug or embedded drug loaded biodegradable microspheres or nanospheres.

The gel material can be topically administered using a needle and syringe or via a squeezable tube/package. For example, a first responder may simply administer the composition to cover the entire wound surface area. This provides a blanketing protective covering over the wound until the patient is further treated.

In certain embodiments, the composition does not have bioadhesive properties. For example, the composition when topically administered to a wound surface does not bioadhere to the wound surface. The composition is retained on the tissue by volume fill, occupying the wound space and/or another topical dressing. The compositions disclosed herein are compatible with a liquid bandage, an eye patch, a fox eye shield, or other typical wound coverage materials. In other embodiments, the composition does have adhesive properties.

Studies at the in vitro and in vivo levels suggest the material is biocompatible and feasible for dermal use.

In certain embodiments, disclosed herein are non-degradable thermoresponsive materials that can be injected into the orbit, including extraconal, intraconal, or subperiosteal of the orbit. Orbit injection does not include intraocular injection. In certain embodiments, the material is a non-degradable hydrogel (e.g., stable for at least 12 months) and thermoresponsive, making it easily injectable prior to quick transition to a more solid gel form that can support the eye in the orbit.

In certain embodiments, the materials exhibit long-term stability. Long term stability studies indicate that the materials should be stable for at least than 12 months. For example, in certain embodiments, the material is a non-degradable material that does not exhibit a deviation or only a minimal deviation (e.g, a deviation of less 5%) in measured solid fraction over a period of at least 12 months. In certain embodiments, the swelling ratio and the transition temperature of the material also remains stable (e.g., do not vary by more than 5%) for at least 12 months so that they remain within acceptable ranges for the material's intended clinical use.

In certain embodiments, the hydrogel can be in the form of a liquid or a gel, preferably a liquid, prior to administration. After administration, the hydrogel can be in a form (liquid, gel or solid) suitable for the intended use. For example, the hydrogel may be a solid that molds into the injected space without compressing or damaging the surrounding normal structures.

In certain embodiments, there may be a significantly reduced or even eliminated need for re-administration of the hydrogel. The thermoresponsive nature of the hydrogel allows for simple removal using irrigation. The hydrogel de-swells (i.e., the volume decreases) upon administration so there is a more controlled gel administration, and removal is much simpler because it can be irrigated and removed as a liquid.

In vitro, ex vivo, and in vivo studies indicate the material is biocompatible and feasible for use intraorbitally.

In addition, this material optionally can be used as an agent delivery platform by combining the hydrogel material with a free agent or an agent-loaded microparticles. This provides a more direct and immediate administration route for example for anti-inflammatory and antibiotic medications. The agent for inclusion in the delivery systems disclosed may be a therapeutic agent, a diagnostic agent, an imaging agent, a cosmetic agent, or other agents.

The option to include an agent-releasing component in the hydrogel makes it particularly useful for the post-injury and pre-surgery time period.

The gels disclosed herein differ from known reconstruction materials for the orbital floor. However, the gels may be compatible for use with these reconstruction materials. Illustrative reconstructions materials include titanium and porous polyethylene (e.g., MEDPOR® implants). These reconstruction materials have their advantages and disadvantages in terms of rate of extrusion and the creation of fibrous tissue that can cause scarring with affects the extraocular muscle function. The gel materials disclosed herein would allow for the natural tissue to heal, achieving long term stability. For example, in certain embodiments the gel material may be degradable over a long time period (e.g., a certain portion (e.g., 1 to 50% solid fraction), but not all, of the material may be made from a biodegradable monomer/crosslinker that biodegrades over a period of at least 12 months).

The gel may be responsive to a stimulus such as, for example, change in temperature, light pH, a triggering molecule concentration (e.g., glucose or an enzyme) or shear stress. In particular embodiments, the gel is a thermoresponsive gel (especially a hydrogel) that responds to external stimulus (e.g., physiological conditions) such as changes in temperature. In certain embodiments, the thermoresponsive hydrogel has a lower critical solution temperature (LCST) below body temperature. The thermoresponsive hydrogel remains fluid below physiological temperature (e.g., 37° C. for humans) or at or below room temperature (e.g., 25° C.), solidify (into a hydrogel) at physiological temperature, and are biocompatible. For example, the thermoresponsive hydrogel may be a clear liquid at a temperature below 34° C. which reversibly solidifies into a gelled composition at a temperature above 34° C. Generally, the LCST-based phase transition occurs upon warming in situ as a result of entropically-driven dehydration of polymer components, leading to polymer collapse. Various naturally derived and synthetic polymers exhibiting this behavior may be utilized. Natural polymers include elastin-like peptides and polysaccharides derivatives, while notable synthetic polymers include those based on poly(N-isopropyl acrylamide) (PNIPAAm), poly (N,N-dimethylacrylamide-co-N-phenylacrylamide), poly (glycidyl methacrylate-co-N-isopropylacrylamide), poly (ethylene oxide)-b-poly(propylene oxide)-b-poly(ethylene oxide), poly(ethylene glycol)-polyester copolymer, and amphiphilic block copolymers. The structure of PNIPAAm, containing both hydrophilic amide bonds and hydrophobic isopropyl groups, leads to a sharp phase transition at the LCST. Studies suggest that the average number of hydrating water molecules per NIPAAm group falls from 11 to about 2 upon the hydrophobic collapse above the LCST (32-34° C.). In certain embodiments, the amphiphilic block copolymer comprises a hydrophilic component selected from poly (dimethylsiloxane), poly ethylene oxide (PEO), poly vinyl alcohol (PVA), poly glycolic acid (PGA), poly (N-isopropylacrylamide), poly(acrylic acid) (PAA), poly vinyl pyrrolidone (PVP) or mixtures thereof, and a hydrophobic component selected from polypropylene oxide (PPO), poly (lactic acid) (PLA), poly(lactic-co-glycolic acid) (PLGA), poly (β-benzoyl L-aspartate) (PBLA), poly (γ-benzyl-L-glutamate) (PBLG), poly (aspartic acid), poly (L-lysine), poly(spermine), poly (ε-caprolactone) or mixtures thereof. Examples of such amphiphilic block copolymers include (PEO)(PPO)(PEO) block copolymers (PEO/PPO), and poly (lactic-co-glycolic acid) block copolymers (PLGA), such as (PEO)(PLGA)(PEO) block copolymers.

In certain embodiments, the gel is non-biodegradable. Illustrative non-biodegradable thermoresponsive gels include PNIPAAm or a copolymer of N-isopropylacrylamide and at least one acrylic and/or methacrylic monomer. In certain embodiments, the Mw of the copolymer may be 5,000-20,000,000 Da. In certain embodiments, the mol % for the N-isopropylacrylamide monomer in the copolymerization reaction may be 50-99 mol %. Illustrative acrylic monomers include an acrylate such as an alkyl acrylate (e.g., methyl acrylate, ethyl acrylate, butyl acrylate or 2-ethylhexyl acrylate), an acrylamide; or an acrylic acid or salt (e.g., 2-ethylacrylic acid, 2-propylacrylic acid, N-acryloxysuccinimide). Illustrative methacrylic monomers include a methacrylate (e.g., 2-hydroxymethacrylate, hydroxyethyl methacrylate, butyl methacrylate, methyl ether methacrylate or methyl methacrylate); a methacrylamide; or a methacrylic acid or salt. In certain embodiments, the acrylate monomer or methacrylate monomer may be modified with poly(ethylene glycol) to provide a co-poly(ethylene glycol) acrylate or co-poly(ethylene glycol) methacrylate prior to reaction with the N-isopropylacrylamide monomer. Acrylated PEG monomer(s) can be added in an amount of 1-15 mol %. In certain embodiments, the mol % for the N-isopropylacrylamide monomer in the copolymerization reaction may be 88-96 mol % and the mol % for the acrylic and/or methacrylic monomer may be 12-4 mol %.

In certain embodiments, the gel is biodegradable over a long time period (e.g., a certain portion (e.g., 1 to 50% w/v solid fraction), but not all, of the material may biodegrade over a period of at least 12 months). Illustrative long-term biodegradable hydrogels include a copolymer of N-isopropylacrylamide and an acrylated lactone, particularly an acrylated γ-butyrolactone (e.g., (R)-α-acryloyloxy-β,β-dimethyl-γ-butyrolactone) or 2-methylene-1,3-dioxepane. The $M_w$ for the resulting copolymer may be 5,000-20,000,000 Da. Acrylated lactone can be added in an amount of 1-15 mol %.

In certain embodiments, an additional crosslinker may be included in the gel copolymer. For example, the crosslinker may be a poly(siloxane) such as an acrylated poly(dimethylsiloxane), a bisacrylamide, a dimethacrylate, a polysaccharide (e.g., an alginate, an acrylated polysaccharide, or a mucopolysaccharide such as chitosan (including a chitosan derivative), hyaluronan, or chondroitin sulfate)), or a combination thereof. The crosslinker can be added in an amount of 0.5-10 mM.

In certain embodiments, a solubility enhancer may be used during synthesis of the gel. For example, poly(ethylene glycol) may be dissolved in the aqueous phase for modulating the rheological properties (the water insoluble gel itself is in a phase separate from the aqueous phase). The solubility enhancer can be added in an amount of 0 to 10% (v/v).

In certain embodiments the composition may include a polysaccharide for providing adhesion to the eye or periocular area. The polysaccharide may be chitosan or a chitosan derivative such as a chitosan salt (e.g., chitosan glutamate, chitosan lactate, chitosan chloride). The amount of the polysaccharide may be 1 mg/mL to 250 mg/mL. In certain embodiments, chitosan or a chitosan salt is included in a blend composition with the copolymer wherein the copolymer is present in an amount of 50% to 90% (w/w), and the chitosan or a chitosan salt is present in an amount of 50 to 10% (w/w).

In certain embodiments the composition may include an alginate for providing in situ crosslinking capabilities to improve stability, adhesion and mechanical properties. An illustrative alginate is sodium alginate crosslinked with a divalent salt, e.g., $Mg^{2+}$, $Ca^{2+}$, $Sr^{2+}$, or $Ba^{2+}$. Divalent cation solutions may be 0.1-20% w/v aqueous solutions. The amount of the alginate may be 1 mg/mL to 25 mg/mL. In certain embodiments, an alginate is included in a blend composition with the copolymer wherein the copolymer is present in an amount of 50% to 90% (w/w), and the alginate is present in an amount of 50 to 10% (w/w).

The composition may be made from a combination or mixture of any of the gels disclosed herein.

Illustrative structures for the gel copolymers include:

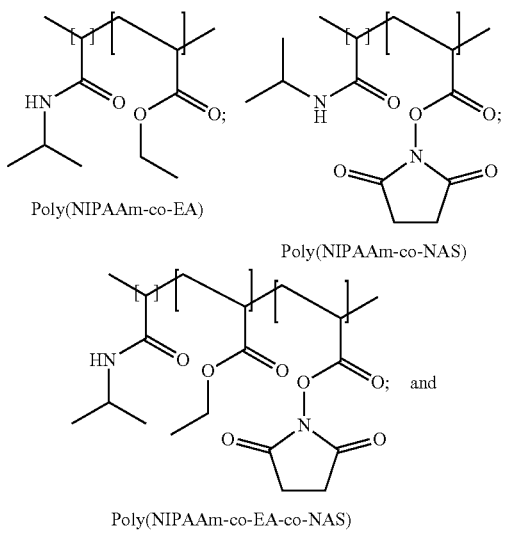

Poly(NIPAAm-co-EA)

Poly(NIPAAm-co-NAS)

Poly(NIPAAm-co-EA-co-NAS)

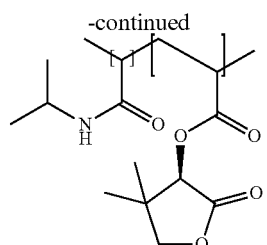

Poly(NIPAAm-co-DBA)

The base precursor (e.g., a prepolymer, oligomer and/or monomer) for the gel, cross linkers, and initiators are mixed together and allowed to polymerize for a predefined period of time (from 1 h to 24 h typically) to form the gel. The gel may then be lyophilized prior to washing or the synthesized gel may be washed directly to remove any excess initiator or unreacted materials. The gel at this stage is a suspension/dispersion/emulsion or a lyophilized solid to which water may be added to reach the desired water content at room temperature until it is ready for use.

The optional agent for inclusion in the delivery systems disclosed may be a therapeutic agent, a diagnostic agent, an imaging agent, a cosmetic agent, or a combination thereof. Illustrative small molecule therapeutic agents that could be used include steroids, corticosteroids, non-steroidal anti-inflammatory drugs (NSAIDs), or antimicrobials including antifungal, antiviral and antibiotic. Particular small molecule therapeutic agents include dexamethasone, ketorolac, moxifloxacin (broader category would be fluoroquinolones), tobramycin, ganciclovir, lidocaine, proparacaine, and betadine. Illustrative biological agents that could be used include antibodies (e.g., infliximab, adalimumab, certolizumab, golimumab, daclizumab, rituximab, basiliximab, efalizumab, alefacept, natalizumab, bevacizumab, ranibizumab), fusion proteins (e.g., etanercept, abatacept, alefacept, anakinra), non-fusion proteins (e.g., chemokines like CCL22; interleukins like IL-2, TNF, or IL-1b; growth factors such as GDNF, NGF; albumin, immunoglobulin, interferons), peptides, or biological milieu (e.g., stem cell conditioned media, plasma, serum).

The agent may be combined with the gel by mixing the agent with the gel. For example, the agent could be loaded in a polymeric matrix (e.g., microparticles, particularly microspheres or nanoparticle, particularly nanospheres). The agent could be provided in a suspension (e.g., a liquid suspension or an aqueous suspension), and the suspension mixed with the gel. If desired, the agent and/or agent-loaded microparticles can be added in before, after, or during the polymerization of the gel to form a suspension of agent or solid microparticles in gel. In certain embodiments, adding microparticles in before or during polymerization results in a slighter faster initial drug release rate.

The agent may be provided in the form of agent-loaded microparticles. The amount of agent-loaded microparticles in the gel may vary, for example from 10:1 or as high as 1000:1 w/v, and more particularly 10 mg/100 ul (100:1 w/v) mixture of microspheres to gel. The polymers for the microparticle may be bioerodible polymers so long as they are biocompatible. Preferred bio-erodible polymers are polyhydroxyacids such as polylactic acid and copolymers thereof. Illustrative polymers include poly(glycolide), poly-lactic acid) (PLA), and poly (lactic-co-glycolic acid) (PLGA). Another class of approved biodegradable polymers is the polyhydroxyalkanoates.

Other suitable polymers include, but are not limited to: polyamides, polycarbonates, polyalkylenes, polyalkylene glycols, polyalkylene oxides, polyalkylene terephthalates, polyvinyl alcohols, polyvinyl ethers, polyvinyl esters, polyvinyl halides, polyvinylpyrrolidone, polyglycolides, polysiloxanes, polyurethanes and copolymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly(ethylmethacrylate), poly(butylmethacrylate), poly(isobutylmethacrylate), poly(hexylmethacrylate), poly(isodecylmethacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene polyethylene glycol), poly(ethylene oxide), poly(ethylene terephthalate), poly(vinyl alcohols), poly(vinyl acetate), poly(vinyl chloride), polystyrene, poly(vinylpyrrolidone), alginate, poly(caprolactone), dextran and chitosan.

The percent loading of an agent may be increased by "matching" the hydrophilicity or hydrophobicity of the polymer to the agent to be encapsulated. In some cases, such as PLGA, this can be achieved by selecting the monomer ratios so that the copolymer is more hydrophilic for hydrophilic drugs or less hydrophilic for hydrophobic drugs. Alternatively, the polymer can be made more hydrophilic, for example, by introducing carboxyl groups onto the polymer. A combination of a hydrophilic drug and a hydrophobic drug can be encapsulated in microparticles prepared from a blend of a more hydrophilic PLGA and a hydrophobic polymer, such as PLA.

A preferred polymer is a PLGA copolymer or a blend of PLGA and PLA. The molecular weight of PLGA is from about 10 kD to about 80 kD, more preferably from about 10 kD to about 35 kD. The molecular weight range of PLA is from about 20 to about 30 kDa. The ratio of lactide to glycolide is from about 75:25 to about 50:50. In one embodiment, the ratio is 50:50.

Illustrative polymers include, but are not limited to, poly(D,L-lactic-co-glycolic acid) (PLGA, 50:50 lactic acid to glycolic acid ratio, $M_n$=10 kDa, acid-terminated, referred to as 502H); poly(D,L-lactic-co-glycolic acid) (PLGA, 50:50 lactic acid to glycolic acid ratio, $M_n$=25 kDa, acid-terminated, referred to as 503H); poly(D,L-lactic-co-glycolic acid) (PLGA, 50:50 lactic acid to glycolic acid ratio, $M_n$=30 kDa, acid-terminated, referred to as 504H); poly(D,L-lactic-co-glycolic acid) (PLGA, 50:50 lactic acid to glycolic acid ratio, $M_n$=35 kDa, ester-terminated, referred to as 504); and poly(D,L-lactic-co-glycolic acid) (PLGA, 75:25 lactic acid to glycolic acid ratio, $M_n$=10 kDa, referred to as 752).

In certain embodiments, the polymer is an ester-terminated PLGA.

In certain embodiments, the polymer is a polyethylene glycol-poly(lactic-co-glycolic acid) copolymer.

In certain embodiments, the polymer microparticles are biodegradable.

The amount of microparticles loaded into the hydrogel may vary. For example, there may be up to 10 mg, more particularly 1 to 5 mg microparticles per microliter hydrogel. In certain embodiments, the microparticles are homogeneously dispersed within the hydrogel. Optional components can be added that allow for easier visualization of the hydrogel/microparticle suspension such as sodium fluorescein or other fluorescent molecules such as FITC, rhodamine, or AlexaFluors or dyes such as titanium dioxide. The water content of the swollen hydrogel at room temperature may be 50-80%. The water content of the hydrogel after it gels in situ in the eye may be 1-10%.

The agent-loaded microparticles may be made, for example, as disclosed in U.S. Patent Application Publication No. 2015-0374633.

The gel disclosed herein may provide for immediate, delayed, or sustained release of an agent. In certain embodiments, an agent that is not encapsulated in a particle may be included in the gel. In such embodiments, the agent release from the gel could be adjusted by modifying the degree of crosslinking. For example, the agent may be released from the gel over a period of one hour to 10 days. In certain embodiments, from 1 ng to 100 mg of an agent may be loaded into the gel.

In certain embodiments, the agent-loaded particle/hydrogel system can provide for a controlled, sustained release over an extended time period. For example, the sustained release may be over a period of at least one day, more particularly at least 5 days or at least 10 days, and most particularly at least 30 days. The agent release can be linear or non-linear (single or multiple burst release). In certain embodiments, the agent may be released without a burst effect. For example, the sustained release may exhibit a substantially linear rate of release of the therapeutic agent in vivo over a period of at least one day, more particularly at least 5 days or at least 10 days, and most particularly at least 30 days. By substantially linear rate of release it is meant that the therapeutic agent is released at a rate that does not vary by more than about 20% over the desired period of time, more usually by not more than about 10%.

It may be desirable to provide a relatively constant rate of release of the agent from the delivery system over the life of the system. For example, it may be desirable for the agent to be released in amounts from 0.1 to 100 µg per day, more particularly 1 to 10 µg per day, for the life of the system. However, the release rate may change to either increase or decrease depending on the formulation of the polymer microparticle and/or gel.

In certain embodiments, the agent release is dependent on degradation of the polymer microparticles. As the polymer chains break up, the agent can diffuse out of the initial polymer microparticle matrix where it will eventually reach the hydrogel matrix. At that point, the hydrogel may partially slow down release of the agent but diffusion through the hydrogel is significantly faster than degradation of the polymer. Thus, the limiting factor in agent release is degradation of the polymer.

The microparticle disclosed herein may provide for controlled release of an agent. The term "controlled release" as used herein, refers to the escape of any attached or encapsulated factor at a predetermined rate. For example, a controlled release of an agent may occur resulting from the predicable biodegradation of a polymer particle (i.e., for example, an artificial antigen presenting cell). The rate of biodegradation may be predetermined by altering the polymer composition and/or ratios comprising the particle. Consequently, the controlled release may be short term or the controlled release may be long term. In one embodiment, the short term release is between 30 minutes-1 hour. In one embodiment, the short term release is between 1 hour-3 hours. In one embodiment, the short term release is between 3 hours-10 hours. In one embodiment, the short term release is between 10 hours-24 hours. In one embodiment, the long term release is between 24 hours-36 hours. In one embodiment, the long term release is between 3 days-7 days. In one embodiment, the long term release is between 7 days-1 month. In one embodiment, the long term release is between 1 month-6 months. In one embodiment, the long term release is between 6 months-1 year. In one embodiment, the long term release is at least one year.

The gel or mixture of gel and microparticles disclosed herein may include an excipient component, such as effective amounts of buffering agents, or antioxidants to protect a drug (the therapeutic agent) from the effects of ionizing radiation during sterilization. Suitable water soluble buffering agents include, without limitation, alkali and alkaline earth carbonates, phosphates, bicarbonates, citrates, borates, acetates, succinates and the like, such as sodium phosphate, citrate, borate, acetate, bicarbonate, carbonate and the like. These agents are advantageously present in amounts sufficient to maintain a pH of the system of between about 2 to about 9 and more preferably about 4 to about 8. As such the buffering agent may be as much as about 5% by weight of the total system. Suitable water soluble preservatives include sodium bisulfate, sodium bisulfate, sodium thiosulfate, ascorbate, benzalkonium chloride, chlorobutanol, thimerosal, phenylmercuric acetate, phenylmercuric borate, phenylmercuric nitrate, parabens, methylparaben, polyvinyl alcohol, benzyl alcohol, phenylethanol and the like and mixtures thereof. These agents may be present in amounts of from 0.001 to about 5% by weight and preferably 0.01 to about 2% by weight.

In certain embodiments, the gel or mixture of gel and microparticles disclosed herein may include (e.g., in an aqueous component of the composition) cell culture media such as Dulbecco's modified Eagle's medium, nutrient mixture F-12 Ham, or a mixture thereof. In certain embodiments, the composition includes both at least one buffering agent and at least one cell culture media.

In certain embodiments, the amount of agent loaded into the microparticles may from 1 ng to 1 mg, more particularly 1 to 100 µg, and most particularly, 20 to 30 µg agent per mg of microparticles. In certain specific embodiments, the amount of agent loaded into the microparticles is 25 to 30 µg agent per mg of microparticles.

In certain embodiments, the polymer microparticles are biodegradable.

The agent-loaded microparticles may have a volume average diameter of 200 nm to 30 µm, more particularly 1 to 10 µm. The agent-loaded microparticles may be pore less or they may contain varying amounts of pores of varying sizes, typically controlled by adding NaCl during the synthesis process.

The agent-loaded microparticle fabrication method can be single or double emulsion depending on the desired encapsulated agent solubility in water, molecular weight of polymer chains used to make the microparticles (MW can range from ~1000 Da to over 100,000 Da) which controls the degradation rate of the microparticles and subsequent drug release kinetics.

The gel materials disclosed herein can be used for treating a variety of ocular pathologies associated with the orbit. For example, the material may be used for providing orbital volume filling and/or mechanical support for the eye. Such orbital volume filling and/or mechanical support may be used for treating enophthalmia, microphthalmia or anophthalmia (repositioning prosthetic eye). The material may be used for delivering an agent(s) for treating inflammation due to trauma or surgery, or prior to orbital floor construction.

The material may be used for delivering an agent(s) for treating infection (bacterial, fungal, or viral). The material may be used for delivering an agent(s) for infection prophylaxis (e.g., post-operatively). The material may be used for delivering an agent(s) for wound healing.

EXAMPLES

Example 1

Synthesis of poly(N-isopropylacrylamide-co-ethyl acrylate) Copolymer

The poly(N-isopropylacrylamide-co-ethyl acrylate) (PNIPAAm-co-EA)) copolymer was synthesized using an ammonium persulfate (APS) and N,N,N',N'-tetramethylethylenediamine (TEMED) redox pair initiated free radical polymerization of N-isopropylacrylamide (NIPAAm) and ethyl acrylate (EA) monomers. Monomers were purified prior to polymerization; NIPAAm was purified via recrystallization in excess n-hexane and MEHQ inhibitor was removed from EA using an inhibitor removal column. 3 g of a PNIPAAm-co-EA copolymer was prepared by dissolving NIPAAm (2.7 g) and EA (327 µL) in 56.64 mL of nanopore water. Once in solution, 300 µL of a 100 mg/mL solution of APS and 120 µL of TEMED were added to initiate polymerization. The reaction proceeded for 16 h at 4° C. The crude polymer was isolated in nanopure water heated to 40° C., flash frozen in liquid $N_2$, and lyophilized for 24 h. Further purification to remove residual vinyl monomer was achieved by dissolving the polymer in tetrahydrofuran (THF) and precipitating (3×) in 10-times excess diethyl ether. The purified polymer was dried under vacuum for 24 h to yield 2.76 g (92%) of a white amorphous solid.

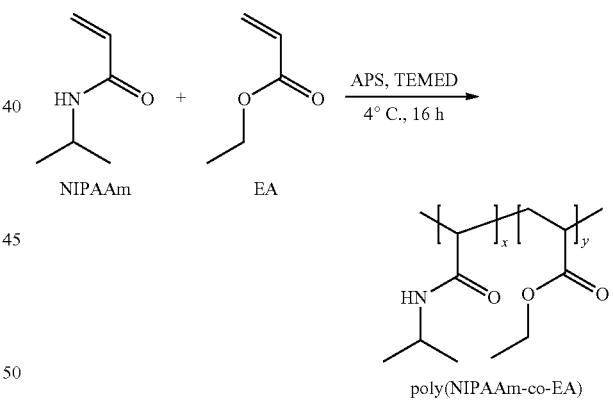

Example 2

Synthesis of poly(N-isopropylacrylamide-co-N-acryloxysuccinimide) Copolymer

The poly(N-isopropylacrylamide-co-N-acryloxysuccinimide) (PNIPAAm-co-NAS) copolymer was synthesized using an ammonium persulfate (APS) and N,N,N',N'-tetramethylethylenediamine (TEMED) redox pair initiated free radical polymerization of N-isopropylacrylamide (NIPAAm) and N-acryloxysuccinimide (NAS) monomers. NIPAAm monomer was purified via recrystallization in excess n-hexane and NAS was used without further purification. 500 mg of a PNIPAAm-co-NAS copolymer was prepared by dissolving NIPAAm (400 mg) and NAS (100 mg) in 9.44 mL of nanopure water. Once in solution, 50 μL of a 100 mg/mL solution of APS and 30 μL of TEMED were added. The polymerization proceeded for 16 h at 4° C. The crude polymer was isolated in nanopure water heated to 40° C., flash frozen in liquid $N_2$, and lyophilized for 24 h. Further purification to remove residual vinyl monomer was achieved by dissolving the polymer in tetrahydrofuran (THF) and precipitating (3×) in 10-times excess diethyl ether. The purified polymer was dried under vacuum for 24 h to yield 450 mg (90%) of a white amorphous solid.

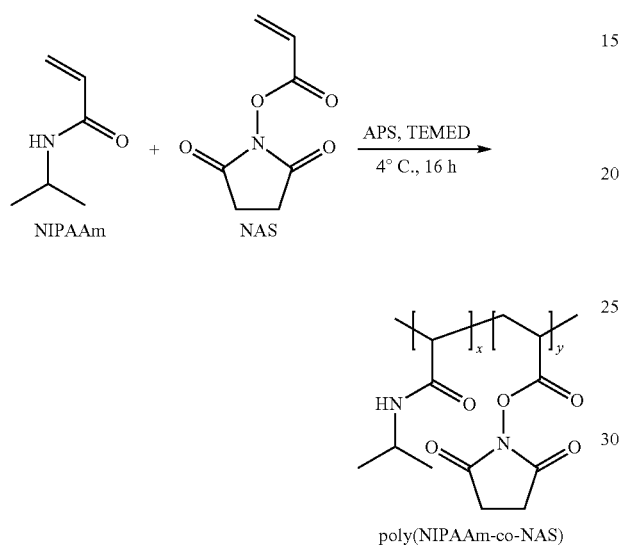

Example 3

Synthesis of poly(N-isopropylacrylamide-co-ethyl acrylate-co-N-acryloxysuccinimide) Copolymer The poly(N-isopropylacrylamide-co-ethyl acrylate-co-N-acryloxysuccinimide) (PNIPAAm-co-EA-co-NAS) copolymer was synthesized using an ammonium persulfate (APS) and N,N,N',N'-tetramethylethylenediamine (TEMED) redox pair initiated free radical polymerization of N-isopropylacrylamide (NIPAAm), ethyl acrylate (EA), and N-acryloxysuccinimide monomers. NIPAAm and EA monomers were purified prior to polymerization; NIPAAm was purified via recrystallization in excess n-hexane and MEHQ inhibitor was removed from EA using an inhibitor removal column, NAS was used as received. 500 mg of a PNIPAAm-co-EA-co-NAS copolymer was prepared by dissolving NIPAAm (410 mg), EA (42.6 μL), and NAS (50 mg, 6.8 mol %) in 9.44 mL of nanopure water. Once in solution, 50 μL of a 100 mg/mL solution of APS and 30 μL of TEMED were added. The polymerization proceeded for 16 h at 4° C. The crude polymer was isolated in nanopure water heated to 40° C., flash frozen in liquid $N_2$, and lyophilized for 24 h. Further purification to remove residual vinyl monomer was achieved by dissolving the polymer in tetrahydrofuran (THF) and precipitating (3×) in 10-times excess diethyl ether. The purified polymer was dried under vacuum for 24 h to yield 470 mg (93%) of a white amorphous solid.

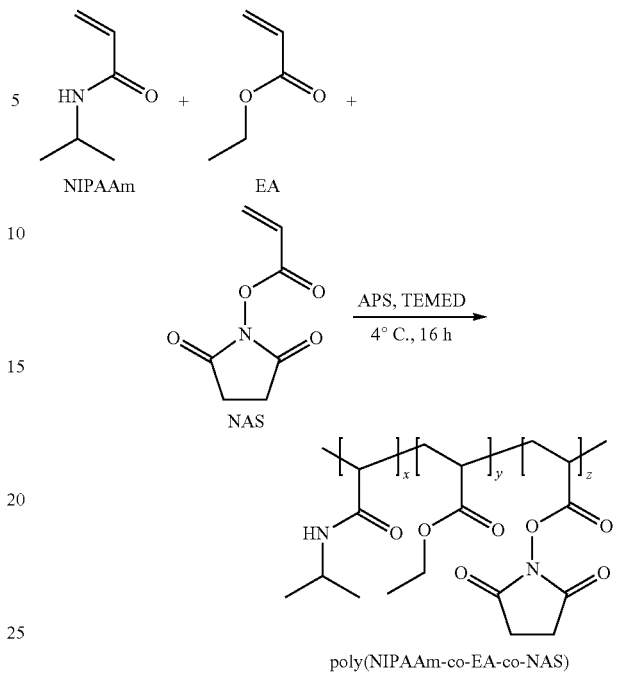

Example 4

Synthesis of poly(N-isopropylacrylamide-co-dimethyl butyrolactone acrylate) Copolymer The poly(N-isopropylacrylamide-co-dimethyl butyrolactone acrylate) (PNIPAAm-co-DBA) copolymer was synthesized using an ammonium persulfate (APS) and N,N,N',N'-tetramethylethylenediamine (TEMED) redox pair initiated free radical polymerization of N-isopropylacrylamide (NIPAAm) and (R)-α-acryloyloxy-β,β-dimethyl-γ-butyrolactone (DBA) monomers. Monomers were purified prior to polymerization; NIPAAm was purified via recrystallization in excess n-hexane and MEHQ inhibitor was removed from DBA via an inhibitor remover column. 500 mg of a PNIPAAm-co-DBA copolymer was prepared by dissolving NIPAAm (410 mg) and DBA (44.4 μL) in 9.44 mL of nanopore water. Once in solution, 50 μL of a 100 mg/mL solution of APS and 30 μL of TEMED were added. The polymerization proceeded for 16 h at 4° C. The crude polymer was isolated in nanopure water heated to 40° C., flash frozen in liquid $N_2$, and lyophilized for 24 h. Further purification to remove residual vinyl monomer was achieved by dissolving the polymer in tetrahydrofuran (THF) and precipitating (3×) in 10-times excess diethyl ether. The purified polymer was dried under vacuum for 24 h to yield 440 mg (88%) of a white amorphous solid.

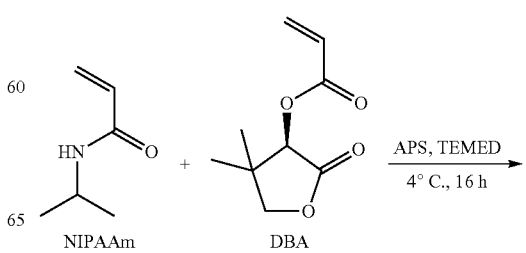

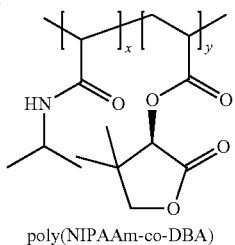

poly(NIPAAm-co-DBA)

In view of the many possible embodiments to which the principles of the disclosed invention may be applied, it should be recognized that the illustrated embodiments are only preferred examples of the invention and should not be taken as limiting the scope of the invention.

What is claimed is:

1. A thermoresponsive gel comprising:
a copolymer of (a) N-isopropylacrylamide and (b) at least one acrylic monomer or at least one methacrylic monomer, wherein the acrylic monomer is an alkyl acrylate, a co-poly(ethylene glycol) acrylate, or an acrylated γ-butyrolactone, and the methacrylic monomer is 2-hydroxymethacrylate, butyl methacrylate, methyl ether methacrylate, methyl methacrylate, or co-poly(ethylene glycol) methacrylate; and
at least one additional additive selected from a poly(siloxane), a bisacrylamide, a dimethacrylate, chitosan, a chitosan derivative, an alginate, an acrylated polysaccharide, hyaluronan, or a combination thereof.

2. The thermoresponsive gel of claim 1, wherein the alkyl acrylate is methyl acrylate, ethyl acrylate, butyl acrylate or 2-ethylhexyl acrylate.

3. The thermoresponsive gel of claim 1, wherein the methacrylic monomer is hydroxyethyl methacrylate, butyl methacrylate, methyl ether methacrylate or methyl methacrylate.

4. The thermoresponsive gel of claim 1, wherein the acrylic monomer is a co-poly(ethylene glycol) acrylate or the methacrylate monomer is a co-poly(ethylene glycol) methacrylate.

5. The thermoresponsive gel of claim 1, wherein the acrylic monomer is an acrylated γ-butyrolactone.

6. The thermoresponsive gel of claim 1, wherein the additional additive is selected from chitosan, a chitosan derivative, an alginate, or a combination thereof.

7. The thermoresponsive gel of claim 1, further comprising dexamethasone.

8. The thermoresponsive gel of claim 1, wherein the copolymer is poly(N-isopropylacrylamide-co-ethyl acrylate) copolymer.

9. The thermoresponsive gel of claim 1, further comprising a therapeutic agent.

10. The thermoresponsive gel of claim 8, wherein the additional additive is an alginate and further comprising a corticosteroid.

11. The thermoresponsive gel of claim 1, wherein the additional additive is an acrylated poly(dimethylsiloxane).

12. The thermoresponsive gel of claim 1, wherein the additional additive is chitosan or a chitosan salt, and wherein the copolymer is present in an amount of 50% to 90% (w/w), and the chitosan or a chitosan salt is present in an amount of 50 to 10% (w/w).

13. The thermoresponsive gel of claim 1, wherein the additional additive is sodium alginate crosslinked with a divalent salt.

14. The thermoresponsive gel of claim 6, wherein the copolymer is poly(N-isopropylacrylamide-co-ethyl acrylate) copolymer.

15. A thermoresponsive gel comprising:
a copolymer of (a) N-isopropylacrylamide and (b) at least one acrylic monomer or at least one methacrylic monomer, wherein the acrylic monomer is a co-poly(ethylene glycol) acrylate or an acrylated γ-butyrolactone, or the methacrylate monomer is a co-poly(ethylene glycol) methacrylate; and
at least one additional additive selected from a poly(siloxane), a bisacrylamide, a dimethacrylate, a polysaccharide, or a combination thereof.

16. The thermoresponsive gel of claim 15, further comprising a therapeutic agent.

17. The thermoresponsive gel of claim 15, wherein the additional additive is selected from chitosan, a chitosan derivative, an alginate, or a combination thereof.

* * * * *